US006846478B1

(12) United States Patent
Doyle et al.

(10) Patent No.: US 6,846,478 B1
(45) Date of Patent: *Jan. 25, 2005

(54) PROMOTING WHOLE BODY HEALTH

(75) Inventors: Matthew Joseph Doyle, Cincinnati, OH (US); Stephen Joseph Hunter-Rinderle, Mason, OH (US); Robert Ernest Singer, Jr., Fairfield, OH (US); Rohan Lalith Wimalasena, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 530 days.

This patent is subject to a terminal disclaimer.

(21) Appl. No.: 09/607,729

(22) Filed: Jun. 30, 2000

Related U.S. Application Data

(60) Continuation-in-part of application No. 09/481,624, filed on Jan. 12, 2000, now Pat. No. 6,264,924, which is a division of application No. 09/032,238, filed on Feb. 27, 1998, now Pat. No. 6,077,502, which is a division of application No. 09/032,237, filed on Feb. 27, 1998, now Pat. No. 6,251,372, which is a division of application No. 09/032,234, filed on Feb. 27, 1998, now Pat. No. 6,132,702.

(51) Int. Cl.$^7$ ............................................... A61K 7/16

(52) U.S. Cl. ............................................................ 424/49

(58) Field of Search ............................. 424/48, 49, 53, 424/440; 426/3

(56) References Cited

U.S. PATENT DOCUMENTS

| 4,599,228 | A | 7/1986 | Ladanyi |  |
|---|---|---|---|---|
| 5,004,597 | A | 4/1991 | Majeti et al. | 424/52 |
| 5,294,433 | A | 3/1994 | Singer et al. | 424/52 |
| 5,364,616 | A | 11/1994 | Singer et al. | 424/52 |
| 5,464,609 | A | 11/1995 | Kelm et al. | 424/54 |
| 5,578,293 | A | 11/1996 | Prencipe et al. | 424/49 |
| 5,639,746 | A | 6/1997 | Yelm | 514/210 |
| 5,646,174 | A | 7/1997 | Kelm et al. | 514/413 |
| 5,672,598 | A | 9/1997 | De et al. | 514/212 |
| 5,753,217 | A | 5/1998 | Christopfel |  |
| 5,785,951 | A | 7/1998 | Kelm et al. | 424/49 |
| 5,830,511 | A | 11/1998 | Mullerat et al. | 424/661 |
| 5,830,915 | A | 11/1998 | Pikul et al. | 514/620 |
| 5,875,798 | A | 3/1999 | Petrus | 132/321 |
| 5,875,799 | A | 3/1999 | Petrus | 132/321 |
| RE36,419 | E | 11/1999 | Cavanaugh, Jr. | 424/54 |
| 6,004,587 | A | 12/1999 | Mullerat et al. | 424/661 |
| 6,015,912 | A | 1/2000 | Wang et al. | 548/408 |
| 6,077,502 | A | 6/2000 | Witt et al. |  |
| 6,132,702 | A | 10/2000 | Witt et al. |  |
| 6,235,269 | B1 | 5/2001 | Witt et al. |  |
| 6,251,372 | B1 | 6/2001 | Witt et al. |  |
| 6,264,924 | B1 * | 7/2001 | Witt et al. | 424/48 |
| 6,350,438 | B1 | 2/2002 | Witt et al. |  |

FOREIGN PATENT DOCUMENTS

| CN | 1075868 | 9/1993 |  |
|---|---|---|---|
| CN | 1103776 | 6/1995 |  |
| CN | 1109742 | 10/1995 |  |
| CN | 1213534 | 4/1999 |  |
| EP | 0 430 474 | 6/1991 |  |
| GB | 2 290233 | 12/1995 |  |
| WO | WO 97 47292 | 12/1997 |  |
| WO | WO 97/47292 | 12/1997 | .......... A61K/31/00 |
| WO | WO 98/08814 | 3/1998 | .......... C07D/207/48 |
| WO | WO 98/08815 | 3/1998 | .......... C07D/207/48 |
| WO | WO 98/08822 | 3/1998 | .......... C07D/239/04 |
| WO | WO 98/08823 | 3/1998 | .......... C07D/239/06 |
| WO | WO 98/08825 | 3/1998 | .......... C07D/241/04 |
| WO | WO 98/17195 | 4/1998 |  |
| WO | WO 98/17237 | 4/1998 | ............ A61K/7/16 |
| WO | WO 98/17270 | 4/1998 | .......... A61K/31/315 |
| WO | WO 99/06340 | 2/1999 |  |
| WO | WO 99/43290 | 9/1999 | ............ A61K/7/16 |
| WO | WO 99/43294 | 9/1999 | ............ A61K/7/20 |
| WO | WO 99/43295 | 9/1999 | ............ A61K/7/20 |

OTHER PUBLICATIONS

"Periodontal Disease and Cardiovascular Disease", *J. Periodontal*, vol. 67, No. 10, 1123–37 (Oct. 1996 Supplement).
"Periodontal Disease and Risk of Cerebrovascular Disease", *Arch Intern Med*, vol. 160, 2749–55 (Oct. 9, 2000).
"Periodontal Disease and Diabetes Mellitus: A Two–Way Relationship", Annals of Periodontology, vol. 3, No. 1, 51–61 (Jul. 1998).
"Role of Periodontitis in Systemic Health: Spontaneous Preterm Birth", *Journal of Dental Education*, vol. 62, No. 10, 852–58 (Oct. 1998).
"Systemic Manifestations of Periodontitis in the Non–Human Primate", *J. Periodontal*, 34, 358–62 (1999).
"Multiple Infections in Carotid Atherosclerotic Plaques", *American Heart Journal*, vol. 138, No. 5, Part 2, 5534–36 (Nov. 1999).
"The Pathogenesis of Human Periodontitis: an Introduction", Periodontology 2000, vol. 14, 9–11 (1997).
"Periodontal Aspects of Systemic Health", *Compendium Contin. Ed. Dentistry*, (190(1), Special issue (1998).

(List continued on next page.)

Primary Examiner—Jon P. Weber
Assistant Examiner—Patricia Patten
(74) Attorney, Agent, or Firm—Emelyn L. Hiland

(57) ABSTRACT

The present invention relates to promoting whole body health in humans and animals by using topical oral compositions comprising a safe and effective amount of chlorite ion in admixture with a pharmaceutically acceptable carrier, said compositions being effective in controlling bacterial-mediated diseases and conditions present in the oral cavity and inhibiting the spread into the bloodstream of oral pathogenic bacteria and associated bacterial toxins and resultant inflammatory cytokines and mediators. The present invention also encompasses methods of use of these compositions by topically applying to the oral cavity, a safe and effective amount of chlorite ion to promote and/or enhance whole body health in humans and other animals.

5 Claims, No Drawings

OTHER PUBLICATIONS

"1997 Sunstar–Chapel Hill Symposium on Periodontal Disease and Human Health: New Directions in Periodontal Medicine", *Ann Periodontology*, 3(1) (Jul., 1998).

"Role of Oral Bacteria in Respiratory Infection", *J. Periodontal.* 70, 793–802 (1999).

"Age, Dental Infections, and Coronary Heart Disease", *J. Dent. Res.*, 7292), 756–60 (2000).

"Association Between Periodontitis and Hypertipidemia: Cause or Effect?," *J. Periodontol.* 70, 1429–34 (1999).

Grossi, S.G., et al., "Treatment of Periodontal Disease in Diabetics Reduces Glycated Hemoglobin", Journal of Periodontology, Aug. 1997, pp. 713–9.

Miller, L.S., et al., "The Relationship Between Reduction in Periodontal Inflammation and Diabetes Control: A Report of 9 Cases", Journal of Periodontology, Oct. 1992, pp. 843–8.

Williams, R.C., et al., Periodontology 2000, vol. 23, Jun. 2000, pp. 9–12.

Limeback, H., "Implication of Oral Infections on Systemic Diseases in the Institutionalized Edlerly with a Special Focus on Pneumonia", Annals of Periodontology, Jul. 1998, pp. 262–75.

DeRiso, A.J., et al., "Chlorhexidine Gluconate 0.12%Oral Rinse Reduces the Incidence of Total Nosocomial Respiratory Infection and Nonprophylactic Systemic Antibiotic Use in Patients Undergoing Heart Surgery", Chest., Jun. 1996, pp. 1556–61.

\* cited by examiner

PROMOTING WHOLE BODY HEALTH

CROSS REFERENCE TO RELATED APPLICATION

This application is a continuation-in-part of application Ser. No. 09/481,624, filed on Jan. 12, 2000, now U.S. Pat. No. 6,264,924, which is a divisional of application Ser. No. 09/032,238, filed on Feb. 27, 1998, now U.S. Pat. No. 6,077,502 issued Jun. 20, 2000; Ser. No. 09/032,237, filed on Feb. 27, 1998, now U.S. Pat. No. 6,251,372, issued Jun. 26, 2001; and Ser No. 09/032,234, file Feb. 27, 1998, now U.S. Pat. No. 6,132,702, issued Oct. 10, 2000.

FIELD OF THE INVENTION

The present invention relates to promoting and enhancing whole body health or overall systemic health in humans and other animals, by use of topical oral compositions comprising an effective amount of chlorite ion, which effectively controls bacterial-mediated diseases and conditions present in the oral cavity and inhibits spread into the bloodstream of pathogenic oral bacteria and associated bacterial toxins and endotoxins as well as the inflammatory cytokines and mediators prompted by these pathogens More particularly, the present invention relates to methods of using the present topical oral compositions to reduce the risk in development of cardiovascular disease, stroke, atherosclerosis, diabetes, severe respiratory infections, premature births and low birth weight, post-partum dysfunction in neurologic and developmental functions, and associated increased risk of mortality by treating and preventing diseases and conditions of the oral cavity.

BACKGROUND OF THE INVENTION

Recent research has revealed that periodontal disease (gum disease) may be a far more serious threat to overall systemic health than previously realized. Periodontitis, a common form of periodontal disease, is a tissue destructive process resulting from the accumulation of pathogenic bacteria along the gingival margin and the consequent tissue destructive host response to these pathogens. The presence of periodontitis can result in the release of pathogenic bacteria and/or bacterial toxins into the bloodstream. The host responses to the presence of these pathogenic bacteria and/or toxins in the bloodstream may contribute to the development of atherosclerosis (heart disease), increase the risk of premature, underweight babies; and pose a serious threat to people whose health is compromised by diabetes, severe respiratory diseases, stroke and bacteremia (bacteria in the blood).

For a long time, it has been known that bacteria may affect the heart. Now evidence is mounting that suggests people with periodontitis, a bacteria-mediated disease, may be more at risk for heart disease, and have a significantly higher risk of having a fatal heart attack, than patients without periodontitis. Heart disease is the leading cause of death in most developed countries, and periodontitis disease is one of the most common bacteria-mediated diseases in humans. Thus even if periodontitis has only a modest effect on increasing the risk of heart attack, its prevalence may make it a significant contributor to the risk for heart disease in the population as a whole.

Several theories exist to explain the link between periodontal disease and heart disease. One theory is that oral pathogenic bacteria enter the blood through inflamed gums, attach to fatty plaques in the coronary arteries (heart blood vessels) and cause small blood clots that contribute to clogged arteries. Researchers have found that 70% of the fatty plaque that blocks carotid arteries and causes stroke contains bacteria. Forty percent of those bacteria have been traced to the mouth. Coronary artery disease is characterized by a thickening of the walls of the coronary arteries due to the buildup of fatty proteins. Blood clots can obstruct normal blood flow, restricting the amount of nutrients and oxygen required for the heart to function properly. This may lead to heart attacks. Another possibility is that changes in systemic inflammatory mediators caused by periodontitis increase development of atherosclerotic plaque, which then contributes to thickening of the arterial walls.

Research also suggests that people with diabetes are more likely to have periodontitis than people without diabetes, and the presence of periodontitis may make it more difficult for diabetics to control their blood sugar. It is known that the presence of periodontitis can increase blood sugar, contributing to increased periods of time when the body functions with a high blood sugar, which puts a diabetic person at increased risk for diabetic complications. Thus, controlling periodontitis may help control diabetes.

A recent study ("Heightened Gingival Inflammation and Attachment Loss in Type 2 Diabetics with Hyperlipidemia," in Journal of Periodontology, November, 1999) found that poorly controlled type 2 diabetic patients are more likely to develop periodontal disease than well-controlled diabetics. In addition, the study further explains why diabetics are more susceptible to severe periodontal disease. The study concluded that poorly controlled diabetics respond differently to bacterial plaque at the gum line than well-controlled diabetics and non-diabetics, possibly due to elevated serum triglycerides. Poorly controlled diabetics have more harmful proteins (cytokines) in their gingival tissue, causing destructive inflammation of the gums. In turn beneficial proteins (growth factors) are reduced, interfering with the healing response to infection. "Increased serum triglyceride levels in uncontrolled diabetics seem to be related to greater attachment loss and probing depths, which are measures of periodontal disease," said Christopher Cutler, D.D.S., Ph.D., the study's lead researcher.

Evidence is also mounting that suggests pregnant women who have periodontitis may be significantly more likely to have a premature, low-birthweight baby. The inflammatory response prompted by periodontitis and/or the associated presence of pathogenic bacteria and bacterial toxins in the bloodstream are cause for concern among pregnant women because they pose a risk to the health of the fetus. The presence of periodontitis appears, to retard fetal growth by releasing into the woman's bloodstream bacterial toxins that reach the placenta and interfere with fetal development by increasing systemic levels of inflammatory mediators that could prompt pre-term birth. Scientists have also proposed that the presence of a low-grade infection may influence harmed cells to discharge inflammatory chemicals, similar to those used to induce abortion, that can cause the cervix to dilate and set off uterine contractions. The risk of having a premature baby of low birth weight was estimated to be at least 7.5 times as high for women with severe periodontal disease, and to occur in 5 percent of pregnancies, costing the U.S. $5.7 billion a year. [Offenbacher S, J. Periodontol. 1996 October;67(10Suppl): 1103–13].

Research further suggests that periodontal disease may pose an increased risk for severe respiratory diseases like pneumonia, bronchitis, emphysema and chronic obstructive pulmonary disease.

The VA Dental Longitudinal Study (DLS) and Normative Aging Study (NAS) examined the relationship of periodontal disease to mortality from all outcomes and concluded that periodontal status at baseline was a significant and independent predictor of mortality.[Annals of Periodontology, 3(1), 33949, July 1998] The study was conducted starting in the mid-1960s among men on good medical health and followed over more than a 25-year period. It was found that for each 20% increment in mean whole-mouth ABL (alveolar bone loss, measured with a Schei ruler using full-mouth series of periapical films), the subject's risk of death increased by 51%. The risk of death was also found to be associated with periodontal status as measured clinically by periodontal probing depth. Subjects in the population group with the deepest average probing depths were found to be at 74% higher risk.

According to Dr. Michael Roizen, University of Chicago internist and anesthesiologist, keeping teeth and gums healthy adds 6.4 years to a person's life. Indeed, the American Academy of Periodontology (AAP) concurs that keeping teeth and gums healthy ranks right up there with taking vitamins, quitting smoking and reducing stress as one of the top things that a person can do to add years to life.

Periodontal disease ("gum disease") is a broad term used to describe those diseases which attack the gingiva and the underlying alveolar bone supporting the teeth. The disease exists in a number of species of warm blooded animals such as humans and canines, and includes a series of diseases exhibiting various syndromes which vary from each other according to the stage or situation of the disease or the age of the patient. The term is used for any inflammatory disease which initially occurs at a marginal gingiva area and may affect the alveolar bone. Periodontal disease affects the periodontium, which is the investing and supporting tissue surrounding a tooth (i.e., the periodontal ligament, the gingiva, and the alveolar bone). Two common periodontal diseases are gingivitis (inflammation of the gingiva) and periodontitis (inflammation of the periodontal ligament manifested by progressive resorption of alveolar bone, increasing mobility of the teeth, and loss of the teeth at advanced stage). Combinations of inflammatory and degenerative conditions are termed periodontitis complex. Other terms used for various aspects of periodontal disease are "juvenile periodontitis", "acute necrotizing ulcerative gingivitis", and "alveolar pyorrhea".

Periodontal disease may involve one or more of the following conditions: inflammation of the gingiva, formation of periodontal pockets, bleeding and/or pus discharge from the periodontal pockets, resorption of alveolar bone, loose teeth and loss of teeth. Periodontal disease is generally considered to be caused by/associated with bacteria which are generally present in dental plaque which forms on the surface of the teeth and in the periodontal pocket. Thus, known methods for treating periodontal disease often include the use of antimicrobials and/or anti-inflammatory drugs.

Alveolar bone resorption is a loss of osseous tissue from the specialized bony structure which supports the teeth. Such resorption has many causes including, but not limited to, natural remodeling following tooth extraction, osseous surgery, periodontal flap surgery, dental implants, scaling and root planing and the progression of periodontal disease.

Periodontal disease is a major cause of tooth loss in adult humans. Tooth loss from periodontal disease is a significant problem beginning at age 35, but even by age 15 it is estimated that about 4 out of 5 persons already have gingivitis and 4 out of 10 have periodontitis. While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

Some of this research has focused on oral care compositions and methods comprising chlorine dioxide or chlorine dioxide generating compounds. Chlorine dioxide is a very strong oxidant and is known as a broad spectrum antimicrobial agent.

The prior art discloses compositions and methods that use chlorine dioxide for the treatment of various oral care conditions. Most of these prior art references teach that the delivery of chlorine dioxide is essential to provide efficacy.

The prior art teaches a variety of ways to deliver chlorine dioxide, in oral care compositions, to the oral cavity. For example, U.S. Pat. No. 4,689,215 issued Aug. 25, 1987; U.S. Pat. No. 4,837,009 issued Jun. 6, 1989; U.S. Pat. No. 4,696,811, issued Sep. 29, 1987; U.S. Pat. No. 4,808,389 issued Feb. 28, 1989; U.S. Pat. No. 4,786,492 issued Nov. 22, 1988; U.S. Pat. No. 4,788,053 issued Nov. 29, 1988; U.S. Pat. No. 4,792,442 issued Dec. 20, 1988; U.S. Pat. No. 4,818,519 issued Apr. 4, 1989; U.S. Pat. No. 4,851,21 issued Jul. 25, 1989; U.S. Pat. No. 4,855,135 issued Aug. 8, 1989; U.S. Pat. No. 4,793,989 issued Dec. 27, 1988; U.S. Pat. No. 4,886,657 issued Dec. 12, 1989; U.S. Pat. No. 4,889,714 issued Dec. 26, 1989; U.S. Pat. No. 4,925,656 issued May 15, 1990; U.S. Pat. No. 4,975,285 issued Dec. 4, 1990; U.S. Pat. No. 4,978,535 issued Dec. 18, 1990; U.S. Pat. No. 5,200,171 issued Apr. 6, 1993; U.S. Pat. No. 5,348,734 issued Sep. 20, 1994; U.S. Pat. No. 5,618,550 issued Apr. 8, 1997, and U.S. Pat. No. 5,489,435 issued Feb. 6, 1996, all to Perry A. Ratcliff, teach oral care compositions and methods of treatment using stabilized chlorine dioxide.

Additional prior art references, which teach the generation and delivery of chlorine dioxide with activator compounds such as protic acids, reducing sugar activators, etc., include: U.S. Pat. No. 5,281,412, Lukacovic et al., issued Jan. 25, 1994, The Procter & Gamble Co.; U.S. Pat. No. 5,110,652, Kross et al., issued Mar. 31, 1992, Alcide Corporation; U.S. Pat. No. 5,019,402, Kross et al., issued May 28, 1991, Alcide; U.S. Pat. No. 4,986,990, Davidson et al., issued Jan. 22, 1991, Alcide; U.S. Pat. No. 4,891,216, Kross et al., issued Jan. 2, 1990, Alcide; U.S. Pat. No. 4,330,531, Alliger, issued May 18, 1982; DE 2,329,753, published Dec. 13, 1973, National Patent Development Corp.; EP 287,074, Kross et al., published Oct. 19, 1988, Alcide; EP 565,134, Kross et al., published Oct. 13, 1993, Alcide; and WO/95/27472, Richter, published Oct. 19, 1995.

Additional prior art references relating to chlorine dioxide compositions include: GB 2,289,841, Mehmet, published Jun. 12, 1995, Janina International; GB 2,290,233, Drayson et al., published Dec. 20, 1995, Medical Express Limited; WO 96/25916, Van Den Bosch et al., published Aug. 29, 1996, Diamond White; JP 054,311, Tsuchikura, published Mar. 28, 1985; JP 105,610, Tsuchikura, published Jun. 11, 1985; and WO/89/03179, Partlow et al., published Apr. 20, 1989, New Generation Products.

In contrast to the prior art relating to chlorine dioxide compositions, the delivery of chlorite ion itself, to the oral cavity to provide efficacy in various oral care conditions has been the focus of WO 99/43290; WO 99/43294; and WO 99/43295, all published Sep. 2, 1999, by the Procter & Gamble Company. The oral care compositions disclosed in these publications comprise chlorite ion wherein no (or only very low levels on chlorine dioxide or chlorous acid is generated or is present in the oral care compositions at the time of use. Moreover, the compositions comprising chlorite ion have relatively alkaline pHs, e.g., pHs above 7 and are specifically designed to avoid or minimize the production of chlorine dioxide or chlorous acid in the compositions. All of the above references are incorporated herein by reference in their entirety.

Another antimicrobial agent that has been incorporated in oral care compositions is stannous ion. The stannous ion generally comes from a stannous salt that is added to a dentifrice. Stannous has been found to help in the reduction of gingivitis, plaque, and sensitivity, and in providing improved breath benefits. The stannous in a dentifrice composition, such as Crest Gum Care will provide efficacy to a subject using the dentifrice, e.g., as a noticeable amount of reduction in gingivitis as measured by the Plaque Glycolysis Regrowth Model (PGRM). Dentifrices containing stannous salts, particularly stannous fluoride and stannous chloride, are described in U.S. Pat. No. 5,004,597 to Majeti et al., incorporated herein in its entirety. Other descriptions of stannous salt dentifrices are found in U.S. Pat. No. 5,578,293.

Additionally, research has focused on oral care compositions comprising agents such as anti-inflammatory agents. The destruction of periodontal tissue is primarily caused by the indirect effects mediated by the host's reaction to the bacteria in the periodontium and gingival sulcus. Bacterial metabolites induce leukocyte chemotaxis which results in the accumulation of inflammatory cells at the site of the bacterial challenge. Furthermore, bacterial metabolites induce the production of inflammatory mediators by leukocytic cells, in particular monocytes. Amongst these are local disease mediators such as metabolites of arachidonic acid, e.g., leukotrienes, prostaglandins and thromboxanes. Additionally, the loss of alveolar bone may be directly induced by pathogenic metabolites of bacteria, in particular proteolytic enzymes. Prostaglandins have been found to be particularly important in the metabolism and destruction of tissue and alveolar bone. Indeed, the production of prostaglandins in the periodontal tissues has been found to be an important mediator of the loss of alveolar bone in the periodontium; patients with periodontal breakdown show an elevated prostaglandin $E_2$ level both in the gingival tissue as well as in the crevicular fluid. Prostaglandins and thromboxanes are formed from arachidonic acid by an enzyme cascade, the first step of which is the cyclo-oxygenation by an enzyme called cyclo-oxygenase. Inhibiting the cyclo-oxygenase would inhibit the formation of prostaglandins and thus reduce alveolar bone loss, and indeed certain cyclo-oxygenase inhibitors, particularly non steroidal anti-inflammatory drugs such as indomethacin and flurbiprofen have been found to markedly reduce the resorption of alveolar bone.

However, as concluded by R. C. Williams and S. Offenbacher in Periodontology 2000, vol. 23, pp. 9–12 (June 2000), no studies have demonstrated the beneficial effects of periodontal therapy compositions on systemic disease outcomes. The authors further report that no periodontal treatment protocols are available that are specifically designed to improve systemic health.

It has now been discovered by the present inventors that topical oral compositions comprising chlorite ion, which are effective in controlling bacterial-mediated diseases and conditions present in the oral cavity and in inhibiting spread into the bloodstream of pathogenic bacteria, associated bacterial toxins and resultant inflammatory cytokines and mediators, are effective in promoting and/or enhancing whole body health in humans and in other animals. The present invention therefore relates to topical oral compositions comprising chlorite ion and methods of use of these topical oral compositions to promote and/or enhance whole body health in humans and other animals.

None of the foregoing references has disclosed or suggested the use of periodontal therapy compositions by topical application to the oral cavity to promote whole body health in humans and other animals, as measured by the above indices. U.S. Pat. Nos. 5,830,511 and 6,004,587, Mullerat, et al., both disclose methods of systemic administration to food animals (such as chickens, turkeys and pigs), of pH-buffered redox-stabilized compositions comprising halide and oxyhalide ions, specifically via the drinking water of the animals. The compositions are said to form free radical oxyhalide intermediates that produce immunostimulatory effects in the animals, which result in their increased ability to fight off possible infections, increased feed utilization, lower mortality, decreased nitrogen excretion and overall enhanced health. U.S. Pat. Nos. 5,875,798 and 5,875,799, both issued Mar. 2, 1999 to Petrus disclose toothpick and dental floss, respectively, impregnated or coated with zinc salts. The zinc containing toothpick and floss formulations are taught to be useful in treating systemic disease via absorption through periodontal tissue of zinc ions into the bloodstream in amounts sufficient to treat the systemic disease. Commonly-owned WO 97/47292, WO 98/17237 and WO 98/17270 relate to methods of preventing or controlling colds and similar minor maladies, such as flu, through the use of an oral composition applied to the gingival or oral mucosal tissue of subjects susceptible to colds. The oral compositions disclosed in these co-pending applications contain an H2-antagonist, stannous gluconate, and zinc citrate salt, respectively as the active ingredient. All of these references are incorporated by reference herein in their entirety.

SUMMARY OF THE INVENTION

The present invention relates to promoting whole body health in humans and animals by using topical oral compositions comprising a safe and effective amount of chlorite ion in admixture with a pharmaceutically acceptable carrier, said compositions being effective in controlling bacterial-mediated diseases and conditions present in the oral cavity and inhibiting the spread into the bloodstream of oral pathogenic bacteria and associated bacterial toxins and resultant inflammatory cytokines and mediators. The present invention also encompasses methods of use of these compositions by topically applying to the oral cavity, a safe and effective amount of chlorite ion to promote and/or enhance whole body health in humans and other animals.

DETAILED DESCRIPTION OF THE INVENTION

The present invention involves topical oral compositions for promoting whole body health in humans and animals, said compositions comprising a safe and effective amount of chlorite ion in admixture with a pharmaceutically acceptable carrier, and effectively controlling bacterial-mediated diseases and conditions present in the oral cavity and inhibiting spread into the bloodstream of pathogenic bacteria, associated bacterial toxins and resultant inflammatory cytokines and mediators. The present invention also encompasses methods of use of these compositions by topical application to the oral cavity, to promote and/or enhance whole body health in humans and other animals. More particularly, the present invention relates to methods of using the present compositions to reduce the risk in the development of cardiovascular disease, stroke, atherosclerosis, diabetes, severe respiratory infections, premature births and low birth weight (as well as postpartum dysfunction in neurologic and developmental functions), and associated risk of mortality. In a preferred method, the present compositions are used to treat and prevent diseases and conditions of the oral cavity including periodontal disease, thereby promoting and/or enhancing enhanced whole body health for the individual being treated, as evidenced by the following health indices or biomarkers:

1) reduction in risk of development of heart attack, stroke, diabetes, respiratory infections, low birth weight infants, and post-partum dysfunction in neurologic/ developmental function and associated increased risk of mortality;
2) reduction in the development of fatty arterial streaks, atherosclerotic plaques, progression of plaque development, thinning of the fibrous cap on atherosclerotic plaques, rupture of atherosclerotic plaques, and the subsequent blood clotting events;
3) reduction in carotid arterial (intimal) wall thickness (e.g., as assessed by ultra-sound techniques)
4) reduction in exposure of blood and systemic circulation to oral pathogens and/or their toxic components, specifically leading to reduction in blood levels of oral bacteria, lipopolysaccharide (LPS) and/or the incidence of oral pathogens and/or components thereof found in arterial plaques, arterial structures, and/or distant organs (e.g., heart, liver, pancreas, kidney);
5) reduction in the exposure of the lower respiratory track to the inhalation of bacterial pathogens and the subsequent development of pneumonias and/or exacerbation of chronic obstructive lung disease;
6) reduction in alterations in circulating hematocrit, hemoglobin, white blood cell count and/or platelet counts;
7) reduction in the incidence of disregulation in blood/ serum levels of inflammatory mediators/cytokines such as TNF-alpha, IL-6, CD-14, and IL-1;
8) reduction in the incidence of disregulation of blood/ serum levels of acute phase reactants including C-reactive protein, fibrinogen, and haptoglobin;
9) reduction in the incidence of disregulation of blood/ serum markers of metabolic disregulation including homocysteine, glycosylated hemoglobin, 8-iso-PGF-2 alpha, and uric acid;
10) reduction in incidence of disregulation of glucose metabolism as typically assessed by impaired glucose tolerance test, increased fasting blood glucose levels, and abnormal fasting insulin levels; and
11) reduction in disregulation of blood lipid levels specifically including blood or serum cholesterol, triglycerides, LDL, HDL, VLDL, Apolipoprotein B, and/or Apolipoprotein A-1.

By "whole body health" as used herein is meant overall systemic health characterized by a reduction in risk of development of major systemic diseases and conditions including cardiovascular disease, stroke, diabetes, severe respiratory infections, premature births and low birth weights (including post-partum dysfunction in neurologic/ developmental function), and associated increased risk of mortality.

By "diseases or conditions of the oral cavity," as used herein, is meant diseases of the oral cavity including periodontal disease, gingivitis, periodontitis, periodontosis, adult and juvenile periodontitis, and other inflammatory conditions of the tissues within the oral cavity, plus caries, necrotizing ulcerative gingivitis, resulting conditions from these diseases such as oral or breath malodor, and other conditions such as herpetic lesions, and infections that may develop following dental procedures such as osseous surgery, tooth extraction, periodontal flap surgery, dental implantation, and scaling and root planing. Also specifically included are dentoalveolar infections, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, Anaerobic Bacteria in Human Diseases, chapter 4, pp 78–104, and chapter 6, pp 115–154 (Academic Press, Inc., NY, 1977), the disclosures of which are incorporated herein by reference in their entirety. The compositions and methods of treatment of the present invention are particularly effective for treating or preventing periodontal disease (gingivitis and/or periodontitis) and resulting breath malodor.

By "topical oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means a sufficient amount of material to provide the desired benefit while being safe to the hard and soft tissues of the oral cavity. The safe and effective amount of chlorite ion or other active agent, will vary with the particular condition being treated, the age and physical condition of the patient being treated, the severity of the condition, the duration of treatment, the nature of concurrent therapy, the specific form (i.e., salt) of chlorite or other active agent employed, and the particular vehicle from which the chlorite or other active agent is applied.

By the term "comprising", as used herein, is meant that various additional components can be conjointly employed in the compositions of this invention as long as the listed materials perform their intended functions.

By the term "carrier", as used herein, is meant a suitable vehicle (including excipients and diluents), which is pharmaceutically acceptable and can be used to apply the present compositions in the oral cavity.

By "dentifrice" as used herein is meant toothpaste, tooth powder, and tooth gel formulations unless otherwise specified.

The present compositions are effective in killing, and/or altering bacterial metabolism, and/or for a period of time suppressing the growth of, microorganisms which cause topically-treatable infections and diseases of the oral cavity, such as plaque, gingivitis, periodontal disease, and herpetic lesions as well as infections that may develop following dental procedures such as osseous surgery, tooth extraction, periodontal flap surgery, dental implantation, and scaling and root planing. While not intending to be bound by theory, the present inventors believe that chlorite ion provides antimicrobial activity, especially selectivity for gram negative anaerobes known to be involved in periodontal disease, such as *P. gingivalis, B. forsythus, A. actinomycetemcomitans, T. denticola, T. socranskii, F. nucleatum*, and *P. intermedia*. The present compositions are also effective against other oral cavity strains such as *L. acidophilus, L. casei, A. viscosus, S. sobrinus, S. sanguis, S. viridans*, and *S. mutans*.

It is believed that oral infections could lead to systemic infection. Bacteria can spread from the mouth into the bloodstream and other parts of the body, thereby putting a person's health at risk. Recent research has found that periodontal infection may contribute to the development of a number of serious conditions including heart disease, diabetes, respiratory diseases and premature, underweight births.

It is now well established that chronic periodontal infection produces a biologic burden of bacterial toxins and inflammatory cytokines that may initiate and exacerbate atherosclerosis and thromboembolic events. Additionally, a known periodontal pathogen, *Porphyromonas gingivalis* has been isolated from arteriosclerotic plaques. Periodontal disease has also been shown to induce episodes of significant bacteremias and thromboembolic events such as myocardial infarction and stroke can occur following bacteremia. Bacteria associated with periodontal disease, *Streptococcus sanguis* and *Porphyromonas gingivalis*, have been demonstrated to cause platelets to aggreggate upon contact with these bacteria. The resultant bacterially-induced platelet agggregates can form the emboli which are responsible for the acute myocardial infarction or stroke.

Without wishing to be bound by theory, it is believed that the present compositions promote overall body health by controlling bacteria-mediated diseases and conditions present in the oral cavity and thus, preventing the spread of bacteria, bacterial toxins and endotoxins and inflammatory mediators/cytokines into the bloodstream and other parts of the body.

In one aspect the present invention relates to topical oral care compositions for humans and other animals, including therapeutic rinses, especially mouth rinses, as well as toothpastes, tooth gels, tooth powders, non-abrasive gels (including subgingival gels), chewing gums, mouth sprays, lozenges (including breath mints), dental implements (such as dental floss and tape), and pet care products (including nutritional supplements, food, drinking water additives, chews or toys), comprising:

(a) a safe and effective amount, preferably a minimally effective amount, of a chlorite ion agent; and
(b) a pharmaceutically-acceptable topical, oral carrier; wherein the final composition is essentially free of chlorine dioxide or chlorous acid and wherein the composition is essentially free of hypochlorite ions or hypochlorite salts and has a final pH greater than 7, preferably greater than 7.5, and even more preferably from about 8 to 12. Preferably the chlorite ion agent is incorporated in the present compositions in an amount to comprise from about 0.02% to about 6.0%, by weight of chlorite ion.

By "essentially free of chlorous acid or chlorine dioxide" as used herein is meant a composition which comprises very low levels, e.g. less than about 2 ppm, preferably less than about 1 ppm of chlorine dioxide or chlorous acid, using known analytical methods for measuring chlorine dioxide or chlorous acid including highly specific electron spin resonance (ESR) spectroscopy.

Preferably, the present compositions further comprise one or more additional therapeutic agents selected from the group consisting of: antimicrobial/antiplaque agents, biofilm inhibiting agents, anti-inflammatory agents (including cyclo-oxygenase inhibitors and lipoxygenase inhibitors), H2-antagonists, metalloproteinase inhibitors, cytokine receptor antagonists, lipopolysaccharide complexing agents, tissue growth factors, immunostimulatory agents, cellular redox modifiers (antioxidants), analgesics, hormones, vitamins, and minerals.

Chlorite Ion Source

The present invention includes chlorite ion as an essential ingredient in the compositions and methods of the present invention. The chlorite ion can come from any type of chlorite salt. Examples include alkali metal chlorites, alkaline earth metal chlorites, and any other transition metals, inner transition metal chlorites and/or polymeric salts. Water soluble chlorite salts are preferred. Examples of suitable metal chlorites include calcium chlorite, barium chlorite, magnesium chlorite, lithium chlorite, sodium chlorite and potassium chlorite. Sodium chlorite and potassium chlorite are preferred. Sodium chlorite is particularly preferred. Mixtures of two or more sources of chlorite may also be used.

For dentifrice compositions of the present invention, the level of chlorite ion is greater than about 0.02%, preferably greater than about 0.4%, more preferably greater than about 0.6%, even more preferably greater than about 0.75%, and most preferably from about 1% to about 2% by weight of the composition.

For mouthrinse compositions of the present invention, the level of chlorite ion is greater than about 0.02%, preferably greater than about 0.075%, more preferably greater than about 0.15%, by weight of the composition.

For lozenge or breath mint compositions of the present invention, the amount of chlorite ion is from about 0.1 mg to about 12 mg, preferably from about 1 mg to about 6 mg, per unit.

For gum compositions of the present invention, the amount of chlorite ion is from about 0.1 mg to about 12 mg, preferably from about 1 mg to about 6 mg, per unit.

For methods of treating or preventing gingivitis, preferably the compositions comprise from about 0.1% to about 6%, of chlorite ion, by weight of the composition.

Chlorite salts are available from various suppliers as sodium chlorite. Sodium chlorite is commercially available as a technical grade powder or flake, and as an aqueous liquid concentrate in a range of concentrations. Example of sources of sodium chlorite include: sodium chlorite available from Aragonesas and from Vulcan. These sources generally have no more than 4% sodium chlorate as well.

Preferably, the source of chlorite ion has high purity, e.g. 70% or greater. Furthermore, preferably the compositions of the present invention are essentially free of hypochlorite metal salt or hypochlorite ion, dichloroisocyanurate, or salts thereof.

Preferably, the level of chlorite ion is measured by gradient separation of inorganic and organic acid anions using Ion Pac ASII exchange column, available from Dionex Corporation, Sunnyvale, Calif.

The final compositions of the present invention preferably comprise low levels of chlorine dioxide or chlorous acid, or are essentially free of chlorine dioxide or chlorous acid (i.e., have less than about 2 ppm, preferably less than about 1 ppm of chlorine dioxide or chlorous acid).

For dual phase compositions the level of chlorine dioxide or chlorous acid is measured within about 2 to 3 minutes after the two phases are mixed together.

Analytical methods to measure the levels of chlorine dioxide or chlorous acid in the compositions of the present invention are known in the art. For example, L. S. Clesceri, A. E. Greenberg, and R. R. Trussel, *Standard Methods for the Examination of Water and Wastewater*, 17$^{th}$ ed., American Public Health Association, Washington, D.C., 1989, pp. 4–75 through 4–83; E. M. Aieta, P. V. Roberts, and M. Hernandez, *J. Am. Water Works Assoc.* 76(1), pp. 64–70 (1984); J. D. Pfaff and C. A. Brockhoff, *J. Am. Water Works Assoc.* 82(4), pp. 192–195 (1990); G. Gordon, W. J. Cooper, R. G. Rice, and G. E. Pacey, *J. Am. Water Works Assoc.* 80(9), pp. 94–108 (1988); D. L. Harp, R. L. Klein, and D. J. Schoonover, *J. Am. Water Works Assoc.* 73(7), pp. 387–389 (1981); G. Gordon, W. J. Cooper, R. G. Rice, and G. E. Pacey, Am. Water Works Assoc. Res. Foundation, Denver, Colo., 1987, pp. 815; E, Lynch, et al., *Free Radical Research*, 26(3), pp. 209–234 (1997), R. S. Keyes and A. M. Bobst in *Biological Magnetic Resonance*, 14, pp. 283–338 (1998). All of these references are incorporated by reference herein in their entirety.

The pH of the final composition (either a single phase or dual phase composition) of the present invention is greater than 7, preferably greater than 7.5, more preferably from 8 to 12; still more preferably the pH is from 9 to 10.

Preferably for mouthwash compositions the pH of the final composition is greater than 7.5, preferably from 8 to 12, more preferably the pH is from 9 to 10.

Preferably for dentifrice compositions the pH of the final composition is greater than 7.5, preferably from 8 to 12, more preferably the pH is from 9 to 10.

For dual phase compositions the pH is measured after the two phases are mixed together, and is not based on the pH of a single phase prior to mixing.

The pH of the final dentifrice composition is measured from a 3:1 aqueous slurry of toothpaste, e.g. 3 parts water to 1 part toothpaste.

Pharmaceutically-Acceptable Excipients

By "pharmaceutically-acceptable excipient" or "pharmaceutically-acceptable oral carrier," as used herein, is meant one or more compatible solid or liquid filler diluents or encapsulating substances which are suitable for topical, oral administration. By "compatible," as used herein, is meant that the components of the composition are capable of being commingled without interaction in a manner which would substantially reduce the composition's stability and/or efficacy for treating or preventing breath malodor, plaque, gingivitis, periodontal disease and to whiten the teeth, according to the compositions and methods of the present invention.

The carriers or excipients of the present invention can include the usual and conventional components of dentifrices (including gels and gels for subgingival application), mouth rinses, mouth sprays, chewing gums, and lozenges (including breath mints) as more fully described hereinafter.

The compositions of the present invention can be dual phase compositions or single phase compositions. The dual phase compositions comprise a first phase and a second phase:

(a) the first phase comprising chlorite ion; and
(b) the second phase comprising a pharmaceutically-acceptable topical, oral carrier and comprising no chlorite.

These dual phase compositions comprise two phases, wherein chlorite ion is placed in a first phase which is to be kept separate from the second phase. The first phase comprising chlorite ion can additionally comprise pharmaceutically-acceptable topical, oral carriers which are compatible with chlorite ion. Preferably the first phase, in addition to chlorite, comprises one (or more) compatible binder, humectant, buffer and/or preservative. Preferably, the second phase, which comprises no chlorite, comprises flavorant, surfactant, fluoride ion, and/or abrasive.

Normally, each phase in these two phase compositions, is in a separate container or in a single container with two chambers. Prior to use of dual phase composition by the consumer, the two phases are combined by coextrusion of the two separate phases, preferably at a 1:1 volume to volume ratio, and the composition is preferably used immediately after preparation, i.e. within about 5 minutes.

The two phases, however, can be combined from about 1 minute to about 1 hour before use, or during the use of the composition.

Dual phase containers are disclosed in U.S. Pat. No. 5,052,590, Ratcliffe, issued Oct. 1, 1991 and U.S. Pat. No. 4,330,531, Alliger, issued May 18, 1982.

In another preferred embodiment, chlorite is substantially anhydrous until just prior to use. For example, preparing a mouth rinse solution just prior to use by dissolving in water, a substantially anhydrous concentrate of chlorite, to the necessary concentration for use in the method of treatments of the present invention.

The choice of a carrier to be used is basically determined by the way the composition is to be introduced into the oral cavity. If a toothpaste (including tooth gels, etc.) is to be used, then a "toothpaste carrier" is chosen as disclosed in, e.g., U.S. Pat. No. 3,988,433, to Benedict, the disclosure of which is incorporated herein by reference (e.g., abrasive materials, sudsing agents, binders, humectants, flavoring and sweetening agents, etc.). If a mouth rinse is to be used, then a "mouth rinse carrier" is chosen, as disclosed in, e.g., U.S. Pat. No. 3,988,433 to Benedict (e.g., water, flavoring and sweetening agents, etc.). Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al., which is incorporated herein by reference; if a chewing gum is to be used, then a "chewing gum carrier" is chosen, as disclosed in, e.g., U.S. Pat. No. 4,083,955, to Grabenstetter et al., which is incorporated herein by reference (e.g., gum base, flavoring and sweetening agents). If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. No. 5,198,220, Damani, issued Mar. 30, 1993, P&G, U.S. Pat. No. 5,242,910, Damani, issued Sep. 7, 1993, P&G, all of which are incorporated herein by reference. Carriers suitable for the preparation of compositions of the present invention are well known in the art. Their selection will depend on secondary considerations like taste, cost, and shelf stability, etc.

The compositions of the present invention may be in the form of non-abrasive gels, including subgingival gels, which may be aqueous or non-aqueous. Aqueous gels generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. The compositions may comprise an anticaries agent (from about 0.05% to about 0.3% as fluoride ion), and an anticalculus agent (from about 0.1% to about 13%).

Subgingival gels according to the present invention may be prepared using a polymer carrier system comprising polymers of various types including those polymer materials which are safe for use in the oral cavity and wounds of a human or other animal. Such polymers are known, including for example polymers and copolymers such as polylactic acid ("PLA"), polyglycolic acid ("PLG"), polylactyl-co-glycolic acid ("PLGA"), polyaminoacids such as polyaspartame, chitosan, collagen, polyalburrin, gelatin and hydrolyzed animal protein, polyvinyl pyrrolidone xanthan and other water soluble gums, polyanhydride, and poly orthoesters. Preferred are polymers and copolymers of polylactic acid ("PLA"), polyglycolic acid ("PLG"), and poly lactylco-glycolic acid ("PLGA"). Particularly preferred polymers useful for the present invention are the copolymers containing mixtures of lactide and glycolide monomers. Lactide monomeric species preferably comprise from about 15% to about 85%, most preferably from about 35% to about 65% of the polymers, while glycolide monomeric species comprise from about 15% to about 85% of the polymer, preferably from about 35% to about 65% on a molar basis. The molecular weight of the copolymer typically lies in the range of from about 1000 to about 120,000 (number average). These polymers are described in detail in U.S. Pat. No. 4,443,430, Apr. 17, 1984, to Mattei incorporated herein by reference in its entirety.

A feature of fluid gel compositions containing certain of such copolymers is their transformation into near solid phase in the presence of an aqueous fluid such as water, aqueous buffers, serum, crevicular fluid, or other body fluid. This is believed to be due to insolubility of the polymer such as poly(lactyl-co-glycolide) copolymer in water, and related aqueous solvents such as may be present in wound or crevicular fluid. Thus, such fluid compositions can be administered conveniently from a syringe-like apparatus, and can be easily retained at the treatment sites after hardening to a near solid. Further, since such polymeric materials do undergo slow degradation via hydrolysis, the chlorite and any other therapeutic agent contained therein continue to release in a sustained manner from the composition and the composition does not need to be surgically removed later.

The polymer carrier system generally comprises from about 1% to about 90% of said polymeric material, preferably from about 10% to about 70%, of the compositions useful for the methods of the present invention. Generally, for the most preferred copolymers containing lactide and glycolide, less polymer is necessary as the amount of lactide goes up. The polymer carrier system also comprises a solvent such as propylene carbonate. This is a material of commerce and is used in the present compositions at a level of from about 25% to about 90%, to form compositions in gel or liquid form.

Preferred compositions of the subject invention may also be in the form of dentifrices, such as toothpastes, tooth gels and tooth powders. Components of such toothpaste and tooth gels generally include one or more of a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Other preferred compositions of the subject invention are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

Other preferred compositions of the subject invention are dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and fast-dissolving solid forms including compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in copending U.S. patent application Ser. No. 08/253,890, filed Jun. 3, 1994, Brideau; U.S. Pat. No. 4,642,903; U.S. Pat. No. 4,946,684; U.S. Pat. No. 4,305,502; U.S. Pat. No. 4,371,516; U.S. Pat. No. 5,188,825; U.S. Pat. No. 5,215,756; U.S. Pat. No. 5,298,261; U.S. Pat. No. 3,882, 228; U.S. Pat. No. 4,687, 662; U.S. Pat. No. 4,642,903. All of these patents are incorporated herein by reference in their entirety.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: The Science and Practice of Pharmacy, $19^{th}$ Ed., Vol. II, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, Peterson et al., issued Dec. 6, 1994, which is herein incorporated by reference in its entirety.

In still another aspect, the invention comprises a dental implement impregnated with a chlorite ion composition. The dental implement comprises an implement for contact with teeth and other tissues in the oral cavity, said implement being impregnated with a safe and therapeutically effective amount of chlorite ion. The dental implement can be impregnated fibers including dental floss or tape, chips or strips and polymer fibers. Dental floss or tape typically comprise from 0.01 mg to 0.1 mg chlorite ion per cm of material. The dental implement can also be a dental tool used for stimulating the periodontal tissue such as a toothpick or rubber tip.

The compositions of the present invention are preferably essentially free of organic solvents. The compositions of the present invention are also preferably essentially free of peroxy compounds.

Types of carriers or oral care excipients which may be included in compositions of the present invention, along with specific non-limiting examples, are:

Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxies, and cross-linked polyesters. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, Zeodent®, particularly the silica carrying the designation Zeodent 119®. The types of silica dental abrasives useful in the toothpastes of the present invention are described in more detail in Wason, U.S. Pat. No. 4,340,583, issued Jul. 29, 1982. The abrasive in the toothpaste compositions described herein is generally present at a level of from about 6% to about 70% by weight of the composition. Preferably, toothpastes contain from about 10% to about 50% of abrasive, by weight of the composition.

A particularly preferred precipitated silica is the silica disclosed in U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued Jul. 29, 1997, all of which are assigned to the Procter & Gamble Co. All of these patents are incorporated herein by reference in their entirety.

Mixtures of abrasives can be used. All of the above patents regarding dental abrasives are incorporated herein by reference. The total amount of abrasive in dentifrice compositions of the subject invention preferably range from about 6% to about 70% by weight; toothpastes preferably contain from about 10% to about 50% of abrasives, by weight of the composition. Solution, mouth spray, mouthwash and non-abrasive gel compositions of the subject invention typically contain no abrasive.

Sudsing Agents (Surfactants)

Suitable sudsing agents are those which are reasonably stable and form foam throughout a wide pH range. Sudsing agents include nonionic, anionic, amphoteric, cationic, zwitterionic, synthetic detergents, and mixtures thereof. Many suitable nonionic and amphoteric surfactants are disclosed by U.S. Pat. No. 3,988,433 to Benedict; U.S. Pat. No. 4,051,234, issued Sep. 27, 1977, and many suitable nonionic surfactants are disclosed by Agricola et al., U.S. Pat. No. 3,959,458, issued May 25, 1976, both incorporated herein in their entirety by reference.

a.) Nonionic and Amphoteric Surfactants

Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed.

The present composition can typically comprise a nonionic, amphoteric, or combination of nonionic and amphoteric surfactant each at a level of from about 0.025% to about 5%, preferably from about 0.05% to about 4%, and most preferably from about 0.1% to about 3%.

b.) Anionic Surfactants

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. The present composition typically comprises an anionic surfactant at a level of from about 0.025% to about 9%, preferably from about 0.05% to about 7%, and most preferably from about 0.1% to about 5%.

Fluoride Ions

The present invention may also incorporate free fluoride ions. Preferred free fluoride ions can be provided by sodium fluoride, stannous fluoride, indium fluoride, and sodium monofluorophosphate. Sodium fluoride is the most preferred free fluoride ion. Norris et al., U.S. Pat. No. 2,946,725, issued Jul. 26, 1960, and Widder et al., U.S. Pat. No. 3,678,154 issued Jul. 18, 1972, disclose such salts as well as others. These patents are incorporated herein by reference in their entirety.

The present composition may contain from about 50 ppm to about 3500 ppm, and preferably from about 500 ppm to about 3000 ppm of free fluoride ions.

Thickening Agents

In preparing toothpaste or gels, it is necessary to add some thickening material to provide a desirable consistency of the composition, to provide desirable chlorite release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Some thickening agents, however, except polymeric polyether compounds, e.g., polyethylene or polypropylene oxide (M.W. 300 to 1,000,000), capped with alkyl or acyl groups containing 1 to about 18 carbon atoms, may react with chlorite. When chlorite is formulated separately in a dual phase composition, preferred thickening agents are hydroxyethyl cellulose and water-soluble salts of cellulose ethers such as sodium carboxymethyl cellulose and sodium carboxymethyl hydroxyethyl cellulose.

A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. No. 5,198,220, Damani, issued Mar. 30, 1993, P&G, U.S. Pat. No. 5,242,910, Damani, issued Sep. 7, 1993, P&G, and U.S. Pat. No. 4,443,430, Mattei, issued Apr. 17, 1984, all of which are incorporated herein by reference.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

Anticalculus Agent

The present invention also includes an anticalculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers

Water employed in the preparation of commercially suitable oral compositions should preferably be of low ion content and free of organic impurities. Water generally comprises from about 5% to about 70%, and preferably from about 20% to about 50%, by weight of the composition herein. These amounts of water include the free water which is added plus that which is introduced with other materials, such as with sorbitol.

Titanium dioxide may also be added to the present composition. Titanium dioxide is a white powder which adds opacity to the compositions. Titanium dioxide generally comprises from about 0.25% to about 5% by weight of the dentifrice compositions.

Other optional agents include synthetic anionic polymeric polycarboxylates being employed in the form of their free acids or partially or preferably fully neutralized water soluble alkali metal (e.g. potassium and preferably sodium) or ammonium salts and are disclosed in U.S. Pat. No. 4,152;420 to Gaffar, U.S. Pat. No. 3,956,480 to Dichter et al., U.S. Pat. No. 4,138,477 to Gaffar, U.S. Pat. No. 4,183,914 to Gaffar et al., and U.S. Pat. No. 4,906,456 to Gaffar et al. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139 (M.W. 500,000), A.N. 119 (M.W. 250,000) and preferably S-97 Pharmaceutical Grade (M.W. 70,000), of GAF Corporation.

Additional Therapeutic Agents

It is recognized that in certain forms of therapy, combinations of therapeutic agents in the same delivery system may be useful in order to obtain an optimal effect. Thus, for example, the present compositions may comprise an additional agent such as antimicrobial/antiplaque agents, biofilm inhibiting agents, anti-inflammatory agents (including cyclo-oxygenase inhibitors and lipoxygenase inhibitors), H2-antagonists, metalloproteinase inhibitors, cytokine receptor antagonists, lipopolysaccharide complexing agents, tissue growth factors, immunostimulatory agents, cellular redox modifiers (antioxidants), analgesics, hormones, vitamins, and minerals. The chlorite ion may be combined with one or more of such agents in a single delivery system to provide combined effectiveness.

Antimicrobial antiplaque agents may include, but are not limited to, triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc ion agents; stannous ion agents; essential oils (including thymol, methyl salicylate, eucalyptol, menthol ) and analogs and salts of the above antimicrobial antiplaque agents. If present, the antimicrobial antiplaque agents generally comprise at least about 0.01% by weight of the compositions of the present invention.

Anti-inflammatory agents may also be present in the oral compositions of the present invention. Such agents may include, but are not limited to, non-steroidal anti-inflammatory agents such as aspirin, ketorolac, flurbiprofen, ibuprofen, naproxen, indomethacin, aspirin, ketoprofen, piroxicam and meclofenamic acid, rofecoxib, celecoxib, and mixtures thereof. If present, the anti-inflammatory agents generally comprise from about 0.001% to about 5% by weight of the compositions of the present invention. Ketorolac is described in USRE 036,419, issued Nov. 30, 1999;

U.S. Pat. No. 5,785,951, issued Jul. 28, 1998 and U.S. Pat. No. 5,464,609, issued Nov. 7, 1995. All of these references are incorporated herein by reference in their entirety.

The present invention can also optionally comprise selective H-2 antagonists preferably selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, ramixotidine, Wy45727, SR-58042, BMY-25405, loxtidine, DA4634, bisfentidine, sufotidine, ebrotidine, HE-30–256, D-16637, FRG-8813, FRG-8701, impromidine, L-643728, and HB408. As used herein, selective H-2 antagonists are compounds which block H-2 receptors, but do not have meaningful. activity in blocking histamine-1 (H-1 or H1) receptors. Topical oral compositions comprising these selective H-2 antagonist compounds are disclosed in U.S. Pat. Nos. 5,294,433 and 5,364,616 Singer et al., issued Mar. 15, 1994 and Nov. 15, 1994 respectively and assigned to The Procter & Gamble Co., which are herein incorporated by reference in their entirety.

If present, the H-2 antagonist agents generally comprise from about from about 0.001% to about 20%, more preferably from about 0.01% to about 15%, more preferably still from about 0.1% to about 10%, still more preferably from about 1% to about 5%, by weight of the compositions of the present invention. Particularly preferred H-2 antagonists include cimetidine, ranitidine, famotidine, roxatidine, nizatidine and mifentidine.

Metalloproteinase inhibitors may also be present in the oral compositions of the present invention. Metalloproteinases (MPs) are enzymes that often act on the intercellular matrix, and thus are involved in tissue breakdown and remodeling and thought to be important in mediating the symptomatology of a number of diseases including periodontal disease. Potential therapeutic indications of MP inhibitors have been discussed in the literature, including treatment of: rheumatoid arthritis (Mullins, D. E., et al., *Biochim. Biophys. Acta*. (1983) 695:117–214); osteoarthritis (Henderson, B., et al., *Drugs of the Future* (1990) 15:495–508); the metastasis of tumor cells (ibid, Broadhurst, M. J., et al., European Patent Application 276,436 (published 1987), Reich, R., et al., 48 *Cancer Res*. 3307–3312 (1988); and various ulcerations or ulcerative conditions of tissue. For example, ulcerative conditions can result in the cornea as the result of alkali burns or as a result of infection by *Pseudomonas aeruginosa*, Acanthamoeba, Herpes simplex and vaccinia viruses. Other examples of conditions characterized by undesired metalloprotease activity include periodontal disease, epidermolysis bullosa, fever, inflammation and scleritis (DeCicco et al., WO 95/29892 published Nov. 9, 1995).

Metalloproteinase inhibitors useful for the present compositions may include, but are not limited to, hydroxamic acid derivatives, phosphinic acid amides, and heteroatom-containing cyclic and acyclic structures such as disclosed in U.S. Pat. No. 6,015,912, issued Jan. 18, 2000; U.S. Pat. No. 5,830,915, issued Nov. 3, 1998; U.S. Pat. No. 5,672,598, issued Sep. 30, 1997 and U.S. Pat. No. 5,639,746, issued Jun. 17, 1997 and in WO 99/52868; WO 99/06340; WO 98/08827; WO98/08825; WO 98/08823; WO 98/08822; WO 98/08815; and WO 98/08814, all assigned to the Procter & Gamble Company and incorporated herein by reference in their entirety. If present, the metalloproteinase inhibitors generally comprise at from about 0.01% to about 5%, by weight of the compositions of the present invention.

Other optional therapeutic agents include antibiotics such as augmentin, amoxicillin, tetracycline, doxycycline, minocycline, metronidazole, neomycin, kanamycin, or clindamycin; immune-suppressive or stimulatory agents such as methotrexate or levamasole; dentinal desensitizing agents such as strontium chloride, potassium nitrate, stannous fluoride or sodium fluoride; odor masking agents such as peppermint oil or chlorophyll; immunostimulatory agents such as immunoglobulin or antigens; local anesthetic agents such as lidocaine or benzocaine; nutritional agents such as amino acids, essential fats, vitamin C and minerals; antioxidants such as alpha-tocopherol (Vitamin E), Co-enzyme Q10, pyrroloquinoline quinone (PQQ), Vitamin C, Vitamin A, folate, N-acetyl cysteine, gallic acid and butylated hydroxy toluene; lipopolysaccharide complexing agents such as polymyxin; peroxides such as urea peroxide; and biofilm inhibiting agents including furanones, cell wall lytic enzymes such as lysozyme, plaque matrix inhibitors such as dextranases and mutanases, and peptides such as bacteriocins, histatins, defensins and cecropins.

Composition Use

A safe and effective amount of the compositions of the present invention and/or chlorite ion may be topically applied to the mucosal tissue of the oral cavity, to the gingival tissue of the oral cavity, and/or to the surface of the teeth, for the treatment or prevention of the above mentioned diseases or conditions of the oral cavity, in several conventional ways. For example, the gingival or mucosal tissue may be rinsed with a solution (e.g., mouth rinse, mouth spray) containing chlorite ion; or if chlorite ion is included in a dentifrice (e.g., toothpaste, tooth gel or tooth powder), the gingival/mucosal tissue or teeth is bathed in the liquid and/or lather generated by brushing the teeth. Other non-limiting examples include applying a non-abrasive gel or paste, which contains chlorite ion, directly to the gingival/mucosal tissue or to the teeth with or without an oral care appliance described below; chewing gum that contains chlorite; chewing or sucking on a breath tablet or lozenge which contains chlorite ion. Preferred methods of applying chlorite ion to the gingival/mucosal tissue and/or the teeth are via rinsing with a mouth rinse solution and via brushing with a dentifrice. Other methods of topically applying chlorite ion to the gingival/mucosal tissue and the surfaces of the teeth are apparent to those skilled in the art.

The concentration of chlorite ion in the composition of the present invention depends on the type of composition (e.g., toothpaste, mouth rinse, lozenge, gum, etc.) used to apply the chlorite ion to the gingival/mucosal tissue and/or the teeth, due to differences in efficiency of the compositions contacting the tissue and teeth, and due also to the amount of the composition generally used. The concentration may also depend on the disease or condition being treated.

It is preferred that the mouth rinse to be taken into the oral cavity have a concentration of chlorite ion in the range of from about 0.02% to about 0.4%, with from about 0.075% to about 0.2% more preferred and from about 0.075% to about 0.15%, by weight of the composition, even more preferred. Preferably mouth rinse compositions of the present invention deliver 3.75 to 22.5 mg of chlorite ion to the oral cavity when approximately 15 ml of the rinse is used.

Mouth sprays preferably have chlorite ion concentrations from about 0.15% to about 5%, with from about 0.2% to about 4% more preferred, with from about 0.75% to about 3.5%, by weight of the composition, even more preferred.

Preferably for dentifrices (including toothpaste and tooth gels) and non-abrasive gels, the concentration of chlorite ion is in the range of from about 0.2% to about 3.0%, by weight of the composition, with from about 0.75% to about 2.5% preferred, and from about 1.5% to about 2%, by weight of the composition, even more preferred.

Chewing gums and lozenges (including breath mints), are generally formulated into compositions of individual unit size preferably containing from about 0.1 mg to about 12 mg, preferably from about 1 mg to about 6 mg, of chlorite ion, per unit used in the oral cavity (i.e. per stick of gum, lozenge, breath mint, etc.).

Pet care products such as foods, chews and toys are generally formulated to contain from 0.2 mg to 200 mg host response modulating agent per unit of product to be administered to the animal. The active agent can be incorporated for example, into a relatively supple but strong and durable material such as rawhide, ropes made from natural or synthetic fibers, and polymeric articles made from nylon, polyester or thermoplastic polyurethane. As the animal chews, licks or gnaws the product, chlorite and any other incorporated active elements are released into the animal's oral cavity into a salivary medium, comparable to an effective brushing or rinsing. Pet food embodiments can be formulated to provide from 0.2 mg to 200 mg active agent per feeding or treating session. The active agent can be incorporated as an ingredient or ad mixed into a pet food such as for example, a kibbled, semi-moist, or canned food. Highly preferred food embodiments include carriers that tend to increase residence time of the food in the oral cavity. For example, the active agent can be incorporated in a carrier that will tend to stick or adhere to the teeth, in order that a certain amount of product will remain in the mouth and not be ingested immediately. The present compositions may also be incorporated into other pet care products including nutritional supplements and drinking water additives.

It should be understood that the present invention relates not only to methods for delivering the present chlorite containing compositions to the oral cavity of a human, but also to methods of delivering these compositions to the oral cavity of other animals, e.g., household pets or other domestic animals, or animals kept in captivity. Other animals include for example, dogs, cats or horses.

For dual- or multi-phase compositions the above concentrations of chlorite ion represent the concentration of chlorite ion after the phases are mixed together, which is usually just prior to use by the consumer. Thus, the concentration of chlorite ion in the chlorite containing phase will vary depending on the amount of the second or additional phases to be mixed with the chlorite-containing phase to obtain the final product for use.

For the method of promoting whole body health of the present invention, by treating diseases or conditions of the oral cavity, a safe and effective amount of chlorite ion is preferably applied to the gingival/mucosal tissue and/or the teeth (for example, by rinsing with a mouthrinse, directly applying a non-abrasive gel with or without a device, applying a dentifrice or a tooth gel with a toothbrush, sucking or chewing a lozenge or breathmint, etc.) preferably for at least about 10 seconds, preferably from about 20 seconds to about 10 minutes, more preferably from about 30 seconds to, about 60 seconds. The method often involves expectoration of most of the composition following such contact. The frequency of such contact is preferably from about once per week to about four times per day, more preferably from about thrice per week to about three times per day, even more preferably from about once per day to about twice per day. The period of such treatment typically ranges from about one day to a lifetime. For particular oral care diseases or conditions the duration of treatment depends on the severity of the oral disease or condition being treated, the particular delivery form utilized and the patient's response to treatment. If delivery to the periodontal pockets is desirable, such as with the treatment of periodontal disease, a mouthrinse can be delivered to the periodontal pocket using a syringe or water injection device. These devices are known to one skilled in the art. Devices of this type include "Water Pik" by Teledyne Corporation. After irrigating, the subject can swish the rinse in the mouth to also cover the dorsal tongue and other gingival and mucosal surfaces. In addition a toothpaste, non-abrasive gel, toothgel, etc. can be brushed onto the tongue surface and other gingival and mucosal tissues of the oral cavity.

The present compositions may also be delivered to tissues and/or spaces within the oral cavity using electromechanical devices such as metering devices, targeted application devices and cleaning or integrated oral hygiene systems.

For treating oral tissue wounds and aiding tissue regeneration, fluid subgingival gel compositions that can be inserted via syringe and either a needle or catheter directly into the areas needing treatment, such as the periodontal cavities, are very useful and convenient. Preferred gel-like fluid compositions are those that transform into near solid phase in the presence of aqueous fluid such as water or crevicular fluid, such gels typically comprising from 0.02% to 6% chlorite in a carrier system comprising a poly(lactyl-co-glycolide) copolymer and solvent such as propylene carbonate. The hardened composition is thus retained at the site of application, and since the polymeric carrier undergoes slow degradation via hydrolysis, the chlorite and any other active agent continue to release in a sustained manner from such compositions.

The following non-limiting examples further describe preferred embodiments within the scope of the present invention. Many variations of these examples are possible without departing from the scope of the invention.

All percentages used herein are by weight of the composition unless otherwise indicated.

EXAMPLES

The following examples are made by conventional processes by mixing the following ingredients.

EXAMPLE 1

Dual Phase Dentifrice

| Dentifrice Phase | | Chlorite Phase | |
| --- | --- | --- | --- |
| Ingredient | Wt. % | Ingredient | Wt. % |
| Water | 20.680 | Sodium Chlorite (80%) | 3.75 |
| Sorbitol (70% Solution) | 18.534 | Carbopol 956[2] | 5.62 |
| Glycerin | 9.000 | Water | 86.89 |
| Sodium Carbonate | 1.000 | Sodium Carbonate | 0.53 |
| Sodium Fluoride | 0.486 | Sodium Bicarbonate | 0.42 |
| Propylene Glycol | 8.000 | Sodium Hydroxide | 2.79 |
| Hydrated Silica | 30.00 | Chlorite phase pH = approximately 10 | |
| Xanthan Gum | 0.500 | | |
| Carboxymethyl Cellulose[1] | 0.400 | Total | 100.00 |
| Sodium alkyl sulfate (27.9% Sol'n) | 8.000 | | |
| Titanium Dioxide | 0.700 | | |
| Sodium Saccharin | 0.600 | | |
| Flavor | 2.000 | | |

EXAMPLE 1-continued

Dual Phase Dentifrice

| Dentifrice Phase | | Chlorite Phase | |
|---|---|---|---|
| Ingredient | Wt. % | Ingredient | Wt. % |
| Methyl Paraben | 0.070 | | |
| Propyl Paraben | 0.030 | | |
| Total | 100.00 | | |

After phases mixed in a 1:1 vol./vol. ratio, pH approximately 8.5 to 9.
[1] Grade 7M8SF from Aqualon.
[2] Available from B. F. Goodrich.

EXAMPLE 2

Dual Phase Dentifrice

| Dentifrice Phase | | Chlorite Phase | |
|---|---|---|---|
| Ingredient | Wt. % | Ingredient | Wt. % |
| Water | 22.180 | Sodium Chlorite (80%) | 3.75 |
| Sorbitol (70% Solution) | 13.534 | Carbopol 956[2] | 3.72 |
| Glycerin | 9.000 | Water | 89.82 |
| Disodium Phosphate | 4.500 | Sodium Carbonate | 0.53 |
| Sodium Fluoride | 0.486 | Sodium Bicarbonate | 0.42 |
| Propylene Glycol | 8.000 | Sodium Hydroxide | 1.76 |
| Hydrated Silica | 30.00 | Chlorite phase pH = approximately 10 | |
| Xanthan Gum | 0.500 | | |
| Carboxymethyl Cellulose[1] | 0.400 | Total | 100.00 |
| Sodium alkyl sulfate (27.9% Sol'n) | 8.000 | | |
| Titanium Dioxide | 0.700 | | |
| Sodium Saccharin | 0.600 | | |
| Flavor | 2.000 | | |
| Methyl Paraben | 0.070 | | |
| Propyl Paraben | 0.030 | | |
| Total | 100.00 | | |

After phases mixed in a 1:1 vol./vol. Ratio, pH approximately 7.5.
[1] Grade 7M8SF from Aqualon.
[2] Available from B. F. Goodrich.

EXAMPLE 3

Single Phase Dentifrice

| Ingredient | Wt. % |
|---|---|
| Water | 64.152 |
| Sodium Chlorite (80%) | 1.875 |
| Sodium Fluoride | 0.243 |
| Hydrated Silica | 25.000 |
| Xanthan Gum | 0.600 |
| Carbomer 956[1] | 0.200 |
| Sodium alkyl sulfate (27.9% Sol'n) | 4.000 |
| Titanium Dioxide | 1.000 |
| Sodium Saccharin | 0.130 |
| Flavor | 1.000 |
| Sodium Hydroxide (50% Sol'n) | 1.800 |
| Total | 100.00 |

[1] Available from B. F. Goodrich.
pH approximately 10.

EXAMPLE 4

Dual Phase Mouthwash

| Mouthwash Phase | | Chlorite Phase | |
|---|---|---|---|
| Ingredient | Wt. % | Ingredient | Wt. % |
| Water | 45.00 | Sodium Chlorite (80%) | 0.50 |
| Glycerin | 19.24 | Water | 98.55 |
| Sodium Bicarbonate | 1.00 | Sodium Carbonate | 0.53 |
| Poloxamer 407 | 0.80 | Sodium Bicarbonate | 0.42 |
| Polysorbate 80 | 0.20 | Total | 100.00 |
| Sodium Saccharin | 0.20 | | |
| Flavor | 0.50 | | |
| Color | 0.06 | | |
| Alcohol | 33.00 | | |
| Total | 100.00 | | |

EXAMPLE 5

Single Phase Mouthwash

| Ingredient | Wt. % |
|---|---|
| Water | 98.80 |
| Sodium Chlorite (80%) | 0.25 |
| Sodium Carbonate | 0.53 |
| Sodium Bicarbonate | 0.42 |
| Total | 100.00 |

EXAMPLE 6

Chlorite Lozenge

| Ingredient | |
|---|---|
| Na Chlorite | 6 mg. Per lozenge |
| Flavor | As desired |
| Magnesium Stearate | 7.5 mg. |
| Stearic Acid | 75 mg. |
| Compressible Sugar | QS 1500 mg. |

EXAMPLE 7

Dry Powder Mouthrinse for Reconstitution

| Ingredient | Weight % |
|---|---|
| Spray Dried Ethanol[1] | 85.38 |
| Sodium Bicarbonate | 5.34 |
| Sodium Chlorite (80%) | 1.60 |
| Tastemaker Spray Dried Spearmint #214487 | 6.40 |
| Aspartame | 0.43 |
| Acesulfame Potassium | 0.85 |
| Total | 100.00 |

[1] 30% load, available from Takasago.

EXAMPLE 8

Dry Powder Mouthrinse for Reconstitution

| Ingredient | Weight % |
|---|---|
| Spray Dried Ethanol[1] | 75.00 |
| Sodium Bicarbonate | 15.72 |
| Sodium Chlorite (80%) | 1.60 |

EXAMPLE 8-continued

Dry Powder Mouthrinse for Reconstitution

| Ingredient | Weight % |
|---|---|
| Tastemaker Spray Dried Spearmint #214487 | 6.40 |
| Aspartame | 0.43 |
| Acesulfame Potassium | 0.85 |
| Total | 100.00 |

[1]30% load, available from Takasago.

Add dry ingredients, listed above, in any order, and mix until achieving a homogeneous mixture. Colorants, to provide color after adding water to the dry mixture, are optional.

To Make Finished Mouthwash:

Example 7

Add 1.874 grams of dry powder blend to 15 ml. of $H_2O$ in a small dose cup with lid. Shake vigorously until solids dissolve, rinse and expectorate.

Example 8

Add 1.874 grams of dry powder blend to 15 ml. of $H_2O$ in small dose cup with lid. Shake vigorously until solids dissolve, rinse and expectorate.

EXAMPLE 9

Non-Abrasive Gel

| Ingredient | Weight % |
|---|---|
| Sodium Chlorite (80%) | 1.875 |
| Carbopol 956[1] | 8.00 |
| Sodium Bicarbonate | 0.84 |
| Sodium Hydroxide (50% Solution) | sufficient to get pH 9 |
| Water | QS 100% |

[1]Available from B. F. Goodrich.

EXAMPLE 10

Non-Abrasive Gel

| Ingredient | Weight % |
|---|---|
| Sodium Chlorite (80%) | 1.875 |
| Carbopol 956[1] | 3.90 |
| Sodium Bicarbonate | 0.84 |
| Sodium Hydroxide (50% Solution) | sufficient to get pH 9 |
| Water | QS 100% |

[1]Available from B. F. Goodrich.

For Examples 9 and 10, disperse the Carbopol in water. Thereafter, add the sodium hydroxide and mix. Then add the sodium bicarbonate and mix. Check the pH and adjust to about pH 9 with sodium hydroxide, if needed. Finally, add the sodium chlorite and mix.

EXAMPLE 11

Sub-Gingival Gel

| Ingredient | Weight % |
|---|---|
| Sodium Chlorite (80%) | 2.0 |
| Poly(lactyl-co-glycolide)/50:50 copolymer | 30.0 |
| Propylene carbonate | 68.0 |
| Total | 100.0 |

The above composition can be prepared by first dissolving the copolymer into the propylene carbonate using a propeller mixer. Powdered sodium chlorite is slowly added and mixed into the polymeric solution to a uniform consistency. The resulting gel like fluid can be inserted into or around the periodontal pocket or gingival region via syringe.

EXAMPLE 12

Oral Spray

| Ingredient | Weight % |
|---|---|
| Sodium Chlorite (80%) | 1.25 |
| Sodium bicarbonate | 0.192 |
| Sodium carbonate | 0.289 |
| Water | QS 100% |

The above spray formulation has a pH of approximately 10. In an animal clinical study conducted among Beagle dogs, 30 ml of the spray solution according to Example 12 was applied evenly throughout the dog's mouth twice daily (n=10). After 9 months, significant reductions in attachment loss were observed in the treated animals compared to those receiving placebo (n=30), i.e., a spray solution containing the same ingredients as Example 12 but without sodium chlorite.

Having thus described the invention in detail, it will be clear to those skilled in the art that various changes may be made without departing from the scope of the invention and the invention is not to be considered limited to what is described in the specification.

What is claimed is:

1. A method of promoting whole body health in human and animal subjects comprising topically administering to the subjects' oral cavity a topical oral composition comprising (a) a safe and effective amount of chlorite ion and (b) a pharmaceutically-acceptable topical, oral carrier;

wherein the final composition is essentially free of chlorine dioxide or chlorous acid and wherein the composition is essentially free of hypochlorite ions or hypochlorite salts and has a final pH greater than 7.

2. A method of promoting whole body health in human and animal subjects according to claim 1 wherein the composition administered to the subjects' oral cavity comprises from about 0.02% to 6.0% chlorite ion, by weight of the final composition.

3. A method of promoting whole body health in human and animal subjects according to claim 1, wherein the composition administered topically to the subjects' oral cavity comprises an additional therapeutic active.

4. A method according to claim 3, wherein said additional therapeutic active is triclosan.

5. A method for promoting whole body health in human and other animal subjects, according claim 1 wherein said composition administered to said subjects, is in a form selected from a mouthrinse, toothpaste, tooth gel, tooth powder, non-abrasive gel, chewing gum, mouth spray, lozenge, and a pet care product.

* * * * *